(12) United States Patent
Essex et al.

(10) Patent No.: US 6,541,609 B2
(45) Date of Patent: Apr. 1, 2003

(54) HIV-2 PEPTIDES

(75) Inventors: Myron E Essex, North Easton, MA (US); Phyllis J Kanki, Carlisle, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 137 days.

(21) Appl. No.: 09/776,888

(22) Filed: Feb. 6, 2001

(65) Prior Publication Data

US 2001/0014470 A1 Aug. 16, 2001

Related U.S. Application Data

(63) Continuation of application No. 08/378,872, filed on Jan. 24, 1995, which is a continuation of application No. 07/984,231, filed on Dec. 1, 1992, now abandoned, which is a continuation of application No. 07/658,460, filed on Feb. 22, 1991, now abandoned, which is a continuation of application No. 07/538,680, filed on Jun. 15, 1990, now abandoned, which is a continuation of application No. 06/844,072, filed on Mar. 26, 1986, now abandoned, which is a continuation-in-part of application No. 06/798,126, filed on Nov. 14, 1985, now abandoned.

(51) Int. Cl.⁷ .................................................. C07K 1/00
(52) U.S. Cl. ........................ 530/350; 530/344; 530/826; 435/5; 435/235.1; 435/974
(58) Field of Search .................... 435/5, 235.1, 974; 530/350, 344, 826

(56) References Cited

U.S. PATENT DOCUMENTS

| | | | |
|---|---|---|---|
| 4,725,669 A | 2/1988 | Essex et al. | 530/322 |
| 4,839,288 A | 6/1989 | Montagnier et al. | 435/235 |
| 5,030,718 A | 7/1991 | Montagnier et al. | 530/387 |
| 5,051,496 A | 9/1991 | Alizon et al. | 530/324 |
| 5,055,391 A | 10/1991 | Montagnier et al. | 435/5 |
| 5,066,782 A | 11/1991 | Montagnier et al. | 530/324 |
| 5,079,342 A | 1/1992 | Alizon et al. | 530/324 |
| 5,268,265 A | 12/1993 | Montagnier et al. | 435/5 |
| 5,306,614 A | 4/1994 | Alizon et al. | 435/5 |
| 5,310,651 A | 5/1994 | Alizon et al. | 435/6 |
| 5,364,933 A | 11/1994 | Montagnier et al. | 530/412 |
| 5,545,726 A | 8/1996 | Alizon et al. | 536/23.1 |
| 5,578,715 A | 11/1996 | Alizon et al. | 536/23.72 |
| 5,580,739 A | 12/1996 | Alizon et al. | 435/7.1 |
| 5,597,896 A | 1/1997 | Montagnier et al. | 530/388.35 |
| 5,770,703 A | 6/1998 | Alizon et al. | 530/395 |
| 5,830,641 A | 11/1998 | Montagnier et al. | 435/5 |
| 5,858,651 A | 1/1999 | Alizon et al. | 435/6 |
| 5,866,319 A | 2/1999 | Alizon et al. | 435/5 |
| 5,889,158 A | 3/1999 | Montagnier et al. | 530/387.1 |
| 5,976,785 A | 11/1999 | Alizon et al. | 435/5 |
| 6,037,165 A | 3/2000 | Montagnier et al. | 435/235.1 |
| 6,048,685 A | 4/2000 | Alizon et al. | 435/5 |
| 6,054,565 A | 4/2000 | Alizon et al. | 536/23.1 |
| 6,162,439 A | 12/2000 | Alizon et al. | 424/208.1 |

FOREIGN PATENT DOCUMENTS

EP  0138667  9/1984  ................. 33/571

OTHER PUBLICATIONS

Ishikawa et al., "Isolation and Characterization of HIV–2 from an AIDS Patient in Ghana", *AIDS* 2: pp. 383–388, (Oct., 1988).

Marx (1988) *Res. News* p. 1243.

Chalifoux et al., "Morphologic Changes in Lymph Nodes of Macaques with an Immunodeficiency Syndrome", *Lab. Invest.*, vol. 51, pp. 22–26 (1984).

Dryden (Nov. 24, 1985) *Washington Post*.

Nau, "Le virus du singe vert est retrouvé chez l'homme", (Nov. 24–25, 1985) *Le Monde* 8.

Saltus, "Scientists report *AIDS* variant, hope on vaccine", *Boston Globe* 1, p. 30.

King, et al., "Histopathologic Changes In Macaques With an Acquired Immunodeficiency Syndrome (AIDS)",*A.J.P. 113*, pp. 382–388, (19830.

Henrickson et al., "Clinical Features of Simian Acquired Immunodeficiency Syndrome (SAIDS) in Rhesus Monkeys", *Lab. Animal Sci.* 34, pp. 140–145 (1984).

Henrickson et al., "Epidemic of Acquired Immunodeficiency in Rhesus Monkeys", *Lancet*, pp. 388–390 (1983).

Letvin et al., "Acquired Immunodeficiency Syndrome in a Colony of Macaque Monkeys", *P.N.A.S. USA*, vol. 80, pp. 2718–2722 (1983).

Hefti et al., "Isolation of a Unique Retrovirus, MNV–1, from Macaca Nemestrine", *Virology* 127, pp. 309–319 (1983).

Daniel et al., "A New Type D Retrovirus Isolated from Macaques with an Immunodeficiency Syndrome", *Science* vol. 223, pp. 602–605 (1984).

Desrosiers et al., "Retrovirus D/New England and Its Relation to Mason–Pfizer Monkey Virus", *J. Virol.* 54, pp. 552–560 (1985).

Bryant et al., "Immunodeficiency in Rhesus Monkeys Associated with the Original Mason–Pfizer Monkey Virus", *J.N.C.I.* vol. 77, No. 4, pp. 957–965 (1986).

(List continued on next page.)

*Primary Examiner*—Jeffrey Stucker
(74) *Attorney, Agent, or Firm*—McDonnell Boehnen Hulbert & Berghoff

(57) ABSTRACT

A substantially pure polypeptide having at least one antigenic determinant that is substantially identical to an antigenic determinant of a protein from a cell line infected with simian T-lymphotrophic virus-III or human T-lymphotrophic virus-IV (HTLV-IV), also known as HIV-2, the protein being selected from: a) a glycoprotein having a molecular weight (m.w.) of about, 160,000 daltons; a glycoprotein having a m.w. of about 120,000 daltons; a gag protein having a m.w. of about 55,000 daltons; a gag protein having a m.w. of about 24,000 daltons; and a glycoprotein having a m.w. of about 32,000 daltons. Also disclosed are various methods of immunoassay using that peptide or antibodies raised to it. Finally, immunoassays for simian specimens are disclosed using peptides that are immunologically cross-reactive with the above-described peptide, or antibodies thereto.

13 Claims, 6 Drawing Sheets

OTHER PUBLICATIONS

Figure 1:
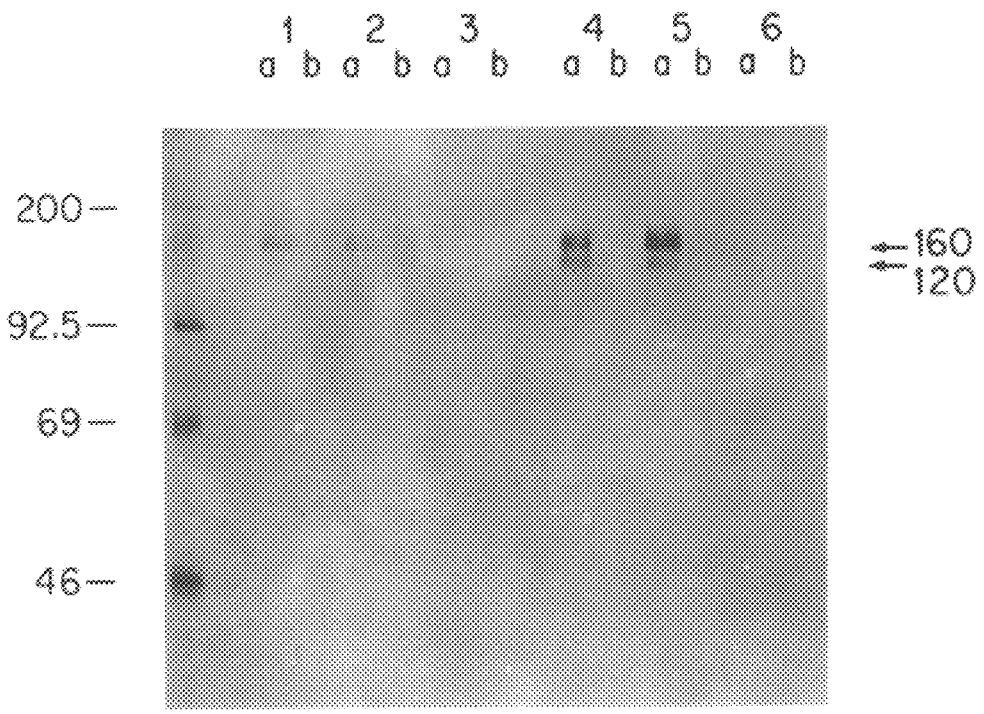

Hunt et al., "Tranmission of Naturally Occuring Lymphoma in Macaque Monkeys", *P.N.A.S. USA* vol. 80, pp. 5085–5089 (1983).
Stromberg et al., "Characterization of Exogenous Type D Retrovirus from a Fibroma of a Macaque with Simian AIDS and Fibromatosis", *Science* 224, pp. 289–292 (1984).
Giddens et al., "Retroperitoneal Fibromatosis and Acquired Immunodeficiency Syndrome in Macaques", *A.M.P.* 119, pp. 253–263 (1985).
London et al., "Experimental Transmission of Simian Acquired Immunodeficiency Syndrome (SAIDS) and Kaposi–Like Skin Lesions", *Lancet*, pp. 869–873 (1983).
Gravell et al., "Transmissio of Simian Acquired Immunodeficiency Syndrome (SAIDS) with Blood or Filtered Plasma", *Science* vol. 223, pp. 74–76 (1983).
Manning et al., "Spontaneous Lymphoma of the Nonhuman Primate", *Lab. Animal Sci.*, vol. 24, pp. 204–210 (1974).
Cleveland, D.W. et al., "Peptide Mapping by Limited Proteolysis in Sodium Dodecyl Sulfate and Analysis by Gel Electrophoresis", *J. Biol. Chem.*, 252, pp. 1102–1106 (1977).
Morgan, M.A. et al., "Structural and Antigenic Analysis of the Nucleic Acid–Binding Proteins of Bovine and Feline Leukemia Viruses", *J. Virol.* vol. 46, No. 1, pp. 177–186 (1983).
Snyder, H.W. et al., *Cold Spring Harbor Symposium Quant. Biol. XLIV*, pp. 787–799 (1980).
Kestler, H. et al., "Comparisons of Simian Immunodeficiency Virus Isolates", *Nature*, 331, pp. 619–621 (1988).
Mulder, C., "A Case of Mistaken Non–Identity", *Nature*, 331, pp. 562–563 (1988).
Desrosiers, R., et al., "Origins of HTLV–4", *Nature*, 327, p. 107 (1987).
Allan, J.S. et al., "Major Glycoprotein Antigens that Induce Antibodies in AIDS Patients are Encoded by HTLV–III", *Science*, vol. 228, pp. 1091–1094 (1985).
European Search Report, EP 86 90 7154 (1986).
Montagnier, et al., "Identification and Antigenicity of the Major Envelope Glycoprotein of Lymphadenopathy–Associated Virus", *Virology*, 144, pp. 283–289 (1985).
Kanki, et al., "Antibodies to Simian T–Lymphotrophic Retrovirus Type III in African Green Monkeys and Recognition of STLV–III Viral Proteins by AIDS and Related Sera", *The Lancet*, pp. 1330–1332 (Jun. 8, 1985).
Kanki, et al., "Serologic Identification and Characterization of a Macaque T–Lymphotropic Retrovirus Closely Related to HTLV–III", *Science*, 228, pp. 1199–1201 (Jun. 7, 1985).
Robey, et al., "Characterization of Envelope and Core Structural Gene Products of HTLV–III with Sera from AIDS Patients", *Science*, vol. 228, pp. 593–595 (May 3, 1985).
Wong–Staal, et al., "Genomic Diversity of Human L–Lymphotropic Virus Type III (HTLV–III)", *Science*, vol. 229, pp. 759–762 (Aug. 23, 1985).
Hahn, et al., "Genomic Diversity of the Acquired Immune Deficiency Syndrome Virus HTLV–III: Different Viruses Exhibit Greatest Divergence in the Envelope Genes", *Proc. Nat'l Acad. Sci., USA*, vol. 82, pp. 4813–4817 (1985).
Yamamoto et al., "Human Adult T–Cell Leukemia Virus is Distinct from a Similar Isolate of Japanese Monkeys", *J. Gen. Vir.*, 65, pp. 2259–2264 (1984).
Daniel, et al., "Isolation of T–Cell Tropic HTLV–III Retrovirus from Macaques", *Science*, pp. 1201–1204 (Jun. 7, 1985).

Kanki, et al., "Isolation of T–Lymphotropic Retrovirus Related to HTLV–III/LAV from Wild–Caught African Green Monkeys",*Science*, 230, pp. 951–954 (Nov. 22, 1985).
Kanki, et al., "New Human T–Lymphotropic Retrovirus Related to Simian T–Lymphotropic Virus Type III (STLV–III$_{AGM}$)", *Science* 232, pp. 238–243 (Apr. 11, 1986).
Poiesz, et al., "Detection and Isolation of Type C Retrovirus Particles from Fresh and Cultured Lymphocytes of a Patient with Cutaneous T–Cell Lymphoma", *Proc. Nat'l Acad. Sci. USA*, vol. 77, No. 12, p. 7415–7419 (1980).
Guo et al., "Novel Viral Sequences Related to Human T–Cell Leukemic Virus in T Cells of a Seropositive Baboon", *Science*, vol. 223, p. 1195–1196 (1984).
Watanabe, et al., "Sequence Homology of the Simian Retrovirus Genome with Human T–Cell Leukemia Virus Type I", *Virology*, vol. 144, p. 59–65 (Jul. 15, 1985).
Popovic, et al., "Detection, Isolation, and Continuous Production of Cytopathic Retroviruses (HTLV–III) from Patients with AIDS and Pre–AIDS", *Science*, vol. 224, p. 497 (1984).
Gallo, et al., "Frequent Detection and Isolation of Cytopathic Retroviruses (HTLV–III) from Patients with AIDS and a Risk for AIDS", *Science*, vol. 224, p. 500–503 (May 4, 1984).
Schüpbach, et al., "Serological Analysis of a Subgroup of Human T–Lymphotropic Retroviruses (HTLV–III) Associated with AIDS", *Science*, vol. 224, p. 503 (1984).
Sarngadharn, et al., "Antibodies Reactive with Human T–Lymphotropic Retroviruses (HTLV–III) in the Serum of Patients with AIDS", *Science*, vol. 224, p. 506–508 (1984).
Kornfeld, et al., *Nature*, vol. 326, pp. 610–613, "Cloning of HTLV–4 and its relation to simian and human immunodeficiency viruses" (Apr. 9, 1987).
Veronese, et al., *Science*, vol. 229, pp. 1402–1405, "Characterization of gp41 as the Transmembrane Protein Coded by the HTLV–III/LAV Envelope Gene" (Jul. 30, 1985).
Fenouillet, et al., *AIDS*, vol. 4, No. 11, pp. 1137–1140, "Early and specific diagnosis of seropositivity to HIVs by an enzyme–linked immunosorbent assay using env–derived synthetic peptides", (1990).
Zvelebil, et al., *FEBS Letters*, vol. 242, No. 1, pp. 9–21, "Predictions of linear T–cell and B–cell eptiopes in proteins encoded by HIV–1, HIV–2 and SIV$_{MAC}$ and the conservation of these sites between strains", (Dec. 1988).
Arya, et al., *Nature*, vol. 328, pp. 548–550, "New human and simian HIV–related retroviruses possess functional transactivator (tat) gene", (Aug. 6, 1987).
Jackson, et al., *The New England Journal of Medicine*, vol. 433, No. 4, pp. 217–222, "Absence of HIV Infection in Blood Donors with Indeterminate Western Blot Tests for Antibody to HIV–1", (Jan. 25, 1990).
Clavel et al., *Science*, vol. 233, pp. 343–346 "Isolation of a New Human Retrovirus from West African Patients with AIDS" (Jul. 18, 1986).
Gnann, et al., *Science*, vol. 237, pp. 1346–1349 "Synthetic Peptide Immunoassay Distinguishes HIV Type 1 and HIV Type 2 Infections"(Sep. 11, 1987).
Gnann, et al., *Journal of Virology*, vol. 61, No. 8, pp. 2639–2641, "Fine Mapping of an Immunodominant Domain in the Transmembrane Gylcoprotein of Human Immunodeficiency Virus" (Aug. 1987).
Hanh, et al., *Nature*, vol. 330, pp. 184–186, "Relation of HTLV–4 to Simian and Human Immunodeficiency–Associated Viruses" (Nov. 12, 1987).

Kanki, et al., *Science*, vol. 228, pp. 1199–1201, "Serologic Identification and Characterization of a Macaque T–Lymphotropic Retrovirus Closely Related to HTLV–III" (Jun. 1985).

Chakrabarti, et al., *Nature*, vol. 328, pp. 543–547, "Sequence of Simian Immunodeficiency Virus from Macaque and its Relationship to other Human and Simian Retroviruses" (Aug. 6, 1987).

Clavel, et al., *Nature* vol. 324, pp. 691–695, "Molecular Cloning and Polymorphism of the Human Immune Deficiency Virus Type 2" (Dec., 1986).

Kanki, et al., *Science*, pp. 827–831, "Human T–Lymphotropic Virus Type 4 and the Human Immunodeficiency Virus in West Africa" (May, 1987).

Daniel, et al., *Science*, pp. 1201–1204, "Isolation of T–Cell Tropic HTLV–III Like Retrovirus from Macaques" (Jun. 1985).

Remold–O'Donnell, "Macrophage Component GP–160 a Major Trypsin Sensitive Surface Glycoprotein", *J. Exp. Med.*, 152(6) (1980), pp. 1699–1708 Abstract Only.

Tokuyama et al., "Cell Surface Major Glycoprotein of BALB/c Mouse Plasmacytoma 58–8 Cells", *J. Natl. Cancer Inst.*, 61(1) (1978), pp. 203–208 Abstract Only.

Owens et al. "A Minor Sialglycoprotein of the Human Erythroctye Membrane" *Arch. Biochem. Biophys.* 204(1): 247–254 (1980).

Castantino–Ceccarini et al., "Further Characterization of HrLa $S_3$ Plasma Membrane Ghosts", *J. Cell. Biol.*, 77(2) (1978), pp. 448–463 Abstract Only.

Strowring et al. "Serological Definition of the Lentiviruses", *J. Virol.* 29: 523–528 (1979).

Gonda et al., "Sequence Homology and Morphological Similarity of HTLV–III and Visna Virus, a Pathogenic Lentivirus", *Science*, 277: 173–177 (1985).

Gogolewski et al. "Antigenic Cross–Reactivity Between Caprine Arthritis–Encephalitits, Visna and Progressive Pneumonia Viruses Involves All Virion–Associated Proteins and Glycoproteins" *J. Gen. Virol.*, 66: 1233–1240 (1985).

Pyper et al., "Sequence Homology Between Cloned Caprine Arthritis Encephalitis Virus and Visna Virus, Two Neutropic Lentiviruses", *J. Virol.* 58: 665 (1986).

Rushlow et al., "Lentivirus Genomic Organization: The Complete Nucleotide Sequence of the ENV Gene Region of Equine Infections Anemia Virus", *Virology*, 155: 309–321 (1986).

Narayan et al., *Biology and Apathogenesis of Lentiviruses of Ruminant Animals*, in: Gallo et al., eds. *Retrovirus Biology and Human Disease*, Marcel Dekker pp. 1117–1146 (1990).

Roitt, "Essential Immunology" *Blackwell Scientific Publications*, Boston p. 191 (1988).

Lerche et al., *J. Nat'l Cancer Inst.* 79: 847–854 (1987) "Natural History Endemic Typed Retrovirus Infection and Acquired Immune Deficiency Syndrome in Group–Housed Rhesus Monkeys".

Barin, F. et al., "Virus Envelope Protein of HTLV–III Represents Major Target Antigen for Antibodies in AIDS Patients", *Science*, vol. 228, pp. 1094–1096 (May 31, 1985).

Neurath, et al., "Radioimmunoassay and Enzyme–Linked Immuoassay of Antibodies to the Core Protein (P24) of Human T–Lymphotropic Virus (HTLV–IIi)", *Jounal of Virological Methods*, 11, pp. 75–86 (1985).

Dowbenko, et al., "Bacterial Expression of the Acquired Immunodeficiency Syndrome Retrovirus p24 Gag Protein and its Use as a Diagnostic Reagent", *Proc. Natl. Acad. Sci. USA*, vol. 82, pp. 7748–7752 (Nov. 1985).

Robey, et al., "Prospect for Prevention of Human Immunodeficiency Virus Infection: Purified 120–kDa Envelope Glycoprotein Induces Neutralizing Antibody", *Proc. Natl. Acad. Sci. USA*, vol. 83, pp. 7023–7027 (Sep. 1986).

Mølbak, et al., "Antibodies to HTLV–IV Associated with Chronic, Fatal Illness Resembling "Slim" Disease", *The Lancet*, pp. 1214–1215 (1986).

Denis, et al., "Efficacy of Five Enzyme Immunoassays for Antibody to HIV in Detecting Antibody to HTLV–IV", *The Lancet*, pp. 324–325 (1987).

Denis, et al., "Prevalence of Human T–Lymphotropic Retroviruses Type III (HIV) and Type IV in Ivory Coast", *The Lancet*, pp. 408–411 (1987).

Kanki, et al., "The Origins of HIV–1 and HTLV–4/HIV–2", *Annals New York Academy of Sciences*, vol. 511, pp. 370–375 (1987).

Albert, et al., "A New Human Retrovirus Isolae of West African Origin (SBL–6669) and its Relationship to HTLV–IV, LAV–II, and HTLV–IIIB", *AIDS Research and Human Retroviruses*, vol. 3, pp. 3–10 (1987).

Kanki, "West African Human Retroviruses Related to STLV–III", *AIDS* 1, pp. 141–145 (1987).

Franchini, et al., "Genetic Analysis of a New Subgroup of Human and Simian T–Lymphotropic Retroviruses: HTLV–IV, LAV–2, SBL–6669, and STLV–III$_{AGM}$", *AIDS Research and Human Retroviruses*, vol. 3, pp. 11–17 (1987).

Ljunggren, et al., "Lack of Cross–Reaction in Antibody–Dependent Cellular Cytotoxicity Between Human Immunodeficiency Virus (HIV) and HIV–Related West African Strains", *The Journal of Immunology*, vol. 140, pp. 602–605 (1988).

Böttiger, et al., "Prevalence of HIV–1 and HIV–2/HTLV–IV Infections in Luanda and Cabinde, Angola", *Journal of Acquired Immune Deficiency Syndromes*, vol. 1, pp. 8–12, (1988).

Palmer, et al., "Ultrastructure of Human Retroviruses", *Journal of Electron Microscopy Technique*, 8:3–15 (1988).

Kanki, et al., "Simian T–Lymphotropic Viruses and Related Human Viruses", *Veterinary Micorbiology*, 17, pp. 309–314 (1988).

Biberfeld, et al., *Enzyme–Immunoassays for the Demonstration of Antibodies to HIV–2$_{SBL-6663}$ and HTLV–IV (SIV$_{MAC}$)*, *AIDS*, 2, pp. 195–199 (1988).

HIV-2 PEPTIDES

CROSS REFERENCE TO RELATED APPLICATIONS

This application claims priority benefit of, and is a continuation of, application Ser. No. 08/378,872, filed Jan. 24, 1995 (pending), which is a continuation of application Ser. No. 07/984,231, filed Dec. 1, 1992 (abandoned), which is a continuation of application Ser. No. 07/658,460, filed Feb. 22, 1991 (abandoned), which is a continuation of application Ser. No. 07/538,680, filed Jun. 15, 1990 (abandoned), which is a continuation of application Ser. No. 06/844,072, filed Mar. 26, 1986 (abandoned), which is a continuation-in-part of application Ser. No. 06/798,126, filed Nov. 14, 1985 (abandoned).

This invention was made with Government support, including NIH research grants CA37466 and CA18216, and National Research Service Award ST32 CA9382. The Government has certain rights in the invention. This application is a continuation-in-part of our commonly owned pending application Ser. No. 798,126, filed Nov. 14, 1985, which is hereby incorporation by reference.

BACKGROUND OF THE INVENTION

This invention relates to primate T-lymphotrophic viruses, as well as assays for such viruses and substances used in those assays.

A group of closely related human retroviruses that preferentially infect helper T-lymphocytes have been designated human T-lymphotrophic viruses (HTLV). One type of HTLV, designated HTLV-I, has been linked with the development of adult T-cell leukemia/lymphoma (Poiesz et al. (1980) Proc. Nat'l. Acad. Sci. USA 77:7415). A virus related to HTLV-I has been reported in non-human primates, specifically Asian and African Old World primate species, but not New World primates and prosimians. The primate viruses from baboons, African green monkeys, and *Macaca* species are related to, yet distinct from, HTLV-I. Guo et al. (1984) Science 223:1195; Tsujimoto et al. (1985) Virology 144:59.

Another type of HTLV, designated variously as HTLV-III, or Lymphadenopathy Associated Virus ("LAV" or "ARV") is the prototype virus from patients with acquired immune deficiency syndrome (AIDS) (Popovic et al. (1984) Science 224:497; Salahuddin et al. (1984) Science 224:500; Schupbach et al. (1984) Science 224:503; Sarngadharn et al. (1984) Science 224:506). Various antigenic proteins from HTLV-III infected cells have been repported, including:

1) a 55 kd gag polyprotein (p55) which yields a 24 kd protein (p24) as the major virus core protein, and a 17 kd phosphoprotein (pp17) (Schupbach et al. (1984) Science 224:503–505); and 2) an envelope glycoprotein (gp160) which gives rise to a 120 kd glycoprotein (gp120) at its amino terminus (Essex and Lee, U.S. Ser. No. 670,361, filed Nov. 9, 1984, and a continuation-in-part thereof filed Nov. 7, 1985, both of which are hereby incorporated by reference).

SUMMARY OF THE INVENTION

We have discovered an exogenous type C retrovirus that infects simian species and is closely related to HTLV-III. Specifically, cells infected woth simian T-lymphotrophic virus-III (STLV-III) produce proteins that are generally immunologically cross-reactive with the respective major proteins produced by HTLV-III infected cells. STLV-III infects African green monkeys (AGM), and *Macaca* species, and may infect other primate species. As used in this application, the term African green monkeys include all animals classified as members of genus *Cercopithecus* and particularly the species *C. aethiops*. Growth characteristics, T-4 tropism, and ultrastructural morphology of STLV-III are similar to that of HTLV-III. The STLV-III that infects *Macaca* species (STLV-III$_{MAC}$) induces biological effects similar to those that HTLV-III induces in humans, including immunodeficiency or immunosuppressive disease. The STLV-III that infects African green monkeys (STLV-III$_{AGM}$) does not appear to produce disease. The term STLV-III is used in this application to include STLV-III$_{AGM}$ and any all forms, subtypes and variations of those and other HTLV-III-like retroviruses that infect simians.

We have also discovered a human virus, HTLV-IV, that is virtually indistinguishable from STLV-III$_{AGM}$ by immunological techniques, and, like STLV$_{AGM}$, does not appear to cause AIDS or ARC-like symptoms in infected humans. The term HTLV-IV is used to designate viruses that immunologically are more closely related to STLV-III than to HTLV-III as indicated by the strength and breadth (number of determinants recognized) of immunological cross reactivity. The term HTLV-IV is used for convenience to refer to human viruses, without necessarily implying any distinction between STLV-III and HTLV-IV.

The discovery and characterization of STLV-III and HTLV-IV is important in several respects. First, STLV-III- and HTLV-IV-infected cells provide a source of antigenic determinants that are generally useful in assays of simian or human specimens, as described below. Second, the animal species particularly at risk for STLV-III infection, the African green monkeys, is used for research and development of a variety of biological reagents; for example African green monkey tissue is used in the production of oral polio vaccine. It is desirable to reduce the chance (however unlikely) that an AIDS-like disease could be transmitted inadvertantly in polio vaccine or other products produced from STLV-III-infected animal tissue. Third, since STLV-III$_{AGM}$ and HTLV-IV do not appear to cause disease in infected monkeys or humans, yet are immunologically cross-reactive with disease-causing HTLV-III, a vaccine based on STLV-III or HTLV-IV could protect against AIDS. Peptides having STLV-III or HTLV-IV antigenic determinants and assays using them Accordingly, a first aspect of the invention generally features a substantially pure polypeptide having at least one antigenic determinant that is substantially identical to an antigenic determinant of a protein from a cell line infected with STLV-III or HTLV-IV, the protein being selected from: a) a glycoprotein having a molecular weight (m.w.) of about 160,000 daltons; a glycoprotein having a m.w. of about 120,000 daltons; a gag protein having a m.w. of about 55,000 daltons; a gag protein having a m.w. of about 24,000 daltons; and a glycoprotein having a m.w. of about 32,000. By "a polypeptide having an antigenic determinant that is substantially identical to a protein antigenic determinant" is meant a polypeptide comprising an antigenic determinant which: a) in common with the protein antigenic determinant, will react with a given antibody; and b) is derived either by i) isolating the naturally produced protein or a fragment of it; or ii) synthesizing (e.g. by expression of DNA such as by the general method of Chang et al. (1985) Nature 315:151, or chemical synthesis) an amino acid sequence identical to the protein antigenic determinant. As demonstrated below, the STLV-III and HTLV-IV cell proteins are immunologically cross-reactive with HTLV-III cell proteins, but the reaction of an STLV-III or HTLV-IV protein with a given antibody may vary in comparison to the reaction of the corresponding HTLV-III protein with the same antibody. Therefore, while the STLV-III and HTLV-IV antigenic determinants may be substantially identical for purposes of this application, neither STLV-III nor HTLV-IV determinants are substantially identical to HTLV-III determinants.

Preferably, the polypeptide antigenic determinant is substantially identical to an antigenic determinant of a protein expressed in a cell line infected with STLV-$III_{AGM}$ or HTLV-IV. Also preferably, the polypeptide is one of the proteins listed above, or a fragment thereof; most preferably, the polypeptide is a gp32 or a gp160 or gp120 glycoprotein in the glycosylated or unglycosylated form. Also preferably, the polypeptide is not substantially cross-reactive with the HTLV-III/LAV glycoprotein p41; and the polypeptide antigenic determinant is more strongly reactive with a determinant of an STLV-III or HTLV-IV glycoprotein than with an HTLV-III glyprotein determinant. Other useful polypeptides which have the necessary immunogenic determinants include synthetic polypeptides.

The above described polypeptides of the first aspect of the invention are useful, among other things, for assaying for the pressure of antibodies to T-lymphotrophic viral antigens, by incubating a specimen with the polypeptide and determining whether or not an immunocomplex is formed. Also, the above-described polypeptides can be used to raise an antibody that is useful for assaying a biological specimen (e.g., human or simian) for the presence of an antigenic determinant that is immunologically cross-reactive with a determinant of one of the four proteins listed above. The assay is performed by incubating the specimen with the antibody thus raised and determining whether an immunocomplex is formed. The determinants to be assayed may occur on the stated proteins themselves or on other polypeptides. They may be in free circulation in the body fluids or in lymphocytes. The assay can be carried out by known immunoassay methods, using antibodies, monoclonal or polyvalent, having immune reactivity with the antigenic determinants found on the stated proteins. For example, competitive immunoassays or immunometric (sandwich) assays can be used. The assays of the first aspect are preferably performed on simian specimens, but they can also be performed on human specimens.

Assays of simian specimens

While the first aspect of the invention features assays that may be conducted on human as well as simian specimens, there is a second aspect of the invention specifically featuring assays on simian specimens. In this aspect, the assay for antibodies to viral antigens can be performed as described above, but a broader class of polypeptides can be used. Thus the second aspect is not limited to assays for antibodies using polypeptides that have an antigenic determinant that is “substantially identical” to the proteins as defined above; the assays use any polypeptide with an antigenic determinant that is immunologically cross-reactive with a determinant of one of the five listed STLV-III or HTLV-IV proteins, regardless of whether the polypeptide determinant is “substantially identical” to the protein determinant.The polypeptides used in the assays of the second aspect include those obtained from cell lines infected with HTLV-III, HTLV-IV, or STLV-III (most preferably STLV-$III_{AGM}$ or HTLV-IV). The polypeptides used in the assays of the second aspect include the glycoproteins (in their glycosylated or unglycosylated form) described in Essex and Lee, U.S. Ser. No. 607,361, filed Nov. 9, 1984 which is hereby incorporated by reference. It has been shown that anti-idiotypic reagents are useful for the detection of antigens carrying sites which are immunologically cross-reactive with those on the antibodies (Potocnjak et al. Science (1982) 215:1637–1639). Thus, such anti-idiotypic antibodies (or immunologically active fragments of them) which can be used as an assay for the presence of antibodies to STLV-III viral antigens; specifically it inlcludes antibodies or fragments thereof which are anti-idiotypic towards the active determinants of STLV-III or HTLV-IV infected cell proteins. Such an anti-idiotypic antibody can be raised against antibodies to the proteins. Preferably, monoclonal antibodies are used.

Also, the second aspect of the invention features assaying simian specimens for an antigenic determinant of a protein of STLV-III as generally described above by incubating the specimen with an antibody (preferably a monoclonal antibody) raised to a polypeptide that is immunologically cross-reactive with one of the five proteins of STLV-III or HTLV-IV infected cells. Preferably, the antibody is raised to protein of a cell infected with STLV-III or HTLV-IV, specifically to gp32, gp120, or gp160 of such a cell.

Vaccines

Finally, in a third aspect, the invention features a vaccine comprising STLV-$III_{AGM}$, HTLV-IV, or a subunit protein or polypeptide therof, such as the gp120, or gp160 or a peptide fraction of those molecules that reacts with HTLV-III, This could be presented in a pharmaceutically acceptable carrier. Vaccine could also comprise proteins from cells infected with STLV-$III_{AGM}$ or HTLV-IV, or an altered form thereof.

Other features and advantages of the invention will be apparent from the following description of the preferred embodiment and from the claims.

DESCRIPTION OF THE PREFERRED EMBODIMENT

We first briefly describe the drawings.

I. Drawings

FIGS. 1–8 are photographs demonstrating immunoprecipitation of various serum samples with preparations of radiolabeled STLV-III or HTLV-IV infected cell lysates with SDS/PAGE.

FIG. 9 is a photograph demonstrating Western blot analysis of STLV-III and HTLV-IV.

II. Obtaining the proteins

The proteins are isolated from cell lines infected with STLV-III or HTLV-IV. The reference STLV-III and HTLV-IV cell lines were derived from co-cultivation of infected lymphocytes and HUT-78 cells. The HUT 78 cell line is a well-characterized mature human T-cell line reported in Gazdar et al. Blood 55:409 (1980); Poiesz et al. Proc. Nat'l. Acad. Sci. USA 77:6815 (1980). Two such HUT-78/STLV-$III_{AGM}$ cell lines have been deposited with the American Type Culture Collection under ATCC Nos. CRL 8942, 8943. An HTLV-IV/HUT-78 cell line is deposited with the ATCC as VR2129.

The preferred proteins are the gp160/120 glycoproteins, which have a molecular weight of approximately 120,000 daltons and 160,000 daltons as determined by sodium dodecyl sulfate polyacrylamide gel electrophoresis (SDS/PAGE), gel electrophoresis, and the proteins are soluble in SDS buffer consisting of 0.15 M sodium chloride, 0.05 M Tris hydrochloride pH 7.2, 1% Triton X-100, 1% sodium deoxycholate, 0.1% sodium dodecylsulfate, and 1 mM phenylmethylsulfonyl fluoride. Triton X-100 is a nonionic detergent (octylphenoxy polyehtoxy (9–10) ethanol). The unglycosylated moiety of the 160,000 dalton glycoprotein has a molecular weight of approximately 90,000 daltons and is immunogenic, sharing some antigenic determinant or determinants with the glycoproteins themselves.

A variety of other cell lines can be infected with STLV-III or HTLV-IV; among them can be mentioned H9 cells, NC37 cells, Molt 3 cells, Molt 4 cells, and CEN cells. It may be that the exact sizes of the novel glycoproteins are slightly different in different lines; however, the common immunologically cross-reactive portion of the glycoproteins is the same regardless of cell line, since it is a protein induced by STLV-III or HTLV-IV. Thus, any cell which harbors the virus may be an appropriate source for the novel glycoproteins.

In order to obtain the protein from any infected cells carrying the virus, the cells are metabolically labelled (e.g. with $^{35}$S-cysteine) and immunoprecipitated with antisera obtained from STLV-III infected animals or HTLV-IV infected humans. The glycoproteins can be prepared with lentil-lectin affinity chromatography from infected cell lysate and subjected to SDS/PAGE. For example, the glycoproteins are present in cell HUT 78/STLV-III- or HTLV-IV-infected cell lines. HUT 78 cells can be infected with fresh virus isolates from infected animals or humans. The glycoproteins can readily be separated from the cells of these cell lines by lysis thereof and SDS gel electrophoresis.

III. Assays

Purified and isolated glyproteins or any antigen immunologically cross-reactive therewith can be employed as a standard antigen in any conventional assay procedure for detection of antibodies specific thereto in biological specimens, and hence detection of the presence in the specimen of cells infected with STLV-III or HTLV-IV.

The glycoproteins or polypeptides immunologically cross-reactive therewith can be labelled by conventional procedures with $^{125}$I or $^{35}$S or $^{3}$H for use in radioimmunoassay, with fluorescein for fluorescent immunoassay, with enzyme for enzyme immunoassay, or with biotin for biotin-avidin inked assays. It can be employed labelled or unlabelled as desired, in competitive immunoassays, as well as in double antibody assays using two antibodies, either of the idiotype:antiidiotype variety or more particularly of the second antibody type using an anti-Fc antibody, or other assays.

Alternatively, the glycoproteins or polypeptides immunologically cross-reaction therewith could be immobilized on an insoluble phase, such as an insoluble resin, and detection of the anti-glycoprotein antibodies is carried out by measuring their binding to the insoluble phase. Insoluble phases also include latex particles, which, when coated with the novel glyprotein or its immunologically cross-reaction polypeptides and subjected to anti-glycoprotein antibody, will agglutinate. Yet other insoluble phases include test tubes, vials, titration wells, and the like, to which the novel glycoprotein or its immunologically cross-reactive polypeptide can be bound, and antibody thereto detected by double antibody techniques or Protein-A dependent techniques.

The assay for antibodies which recognizes STLV-III- or HTLV-IV-induced cell surface antigens may utilize the glycoprotein or glycoproteins or the unglycosylated moiety of MW 120,000 daltons, 160,000 daltons and 90,000 daltons respectively in crude form, and is not limited to using these proteins in substantially pure form. For example, the glycoprotein(s) may be first substantially purified and then mixed together. Alternatively cruder mixtures can also be used.

The elements necessary for carrying out the diagnostic methodology described hereinbefore may be present in a kit. Such kit comprises a carrier being compartmentalized to receive therein one or more containers, which of said containers comprising one or more elements necessary to carry out the tests.

For example, the first container may contain one or both of the purified glycoproteins or its immunologically cross-reactive polypeptides in detectably labelled or in insolubilized form.

A second container may comprise anti IgG antibody, polyclonal or monoclonal, useful in double antibody binding assay, or elements needed for detection of the label on the glycoprotein or its immunogically cross-reactive polypeptides (e.g. chromogenic substrates).

Additional containers may comprise varying amounts of one of the glycoproteins or its immunologically cross-reactive polypeptides which can be used to prepare a standard curve into which experimental results can be interpolated. The materials may be present in the kit by themselves, in solution, freeze-dried, or in admixture with other insert materials, such as inert proteins, and the like.

The biological specimens tested may include blood, serum, lymphocytes, urine, tissues, saliva, feces, and the like. Of particular interest is the screening of blood or other tissue of African green monkeys to be used in vaccine production.

The following specific examples are intended to illustrate more fully the nature of the invention withou acting as a limitation upon its scope.

Examples 1 and 2: Assay of STLV-infected macaque serum with STLV-III antigens

FIG. 1 shows the reactivity of various simian serum samples with the glycoprotein preparation of HUT-78/STLV-III$_{MAC}$ (lane a) and uninfected control HUT-78 (lane b). The glycoproteins are prepared from soluble cell lysates of the cells made with RIPA buffer as described below for FIG. 2, lacking sodium deoxycholate. The lysates are passed through a lentil—lectin—Sepharose Cl-4B (Pharmacia, Sweden) column at a ratio of $20\times10^6$ cells to 1 to 2 ml of undiluted lentil—lectin—Sepharose Cl-4B. The glycoproteins are eluted from the column with a buffer [0.15 M NaCl, 0.05 M tris-HCl, pH 7.2, 1% Triton X-100, and 0.2 methyl-α-D-mannoside]. The eluted bound fraction is reacted with 10 μl test sera that have been reacted to protein A beads (for example used in the general technique of Essex et al. [1983] Science 220:859). The sera used are: Lanes 1 and 2-human reference HTLV-III, positive serum; Lane 3--human reference HTLV-III, negative serum; Lanes 4 and 5--STLV-III positive macaque serum; Lane 6--STLV-III negative macaque serum. The immunoprecipitates are eluted from protein A beads boiling at 100° C. for 2 min. [sample buffer: 0.1 Cleland's reagent; 2% SDS; 0.08 M tris-HCl; pH 6.8; 10 percent glycerol; 0.2% bromophenol blue.] Samples are analyzed by SDS/PAGE in a 10.0 percent acrylamide resolving gel with a 3.5 percent stacking gel according to the discontinuous buffer system of Laemnili (1970) Nature (London) 227:680.

In FIG. 2, HUT-78/STLV-III$_{MAC}$ (lanes a) and HUT-78 (lanes b) are harvested at their peak of log-phase growth and are exposed to [$^{35}$S] cysteine [150 μCi/ml; specific activity, 1000 to 1050 Ci/mmole; New England Nuclear] for 8–10 hours. A soluble cell lysate is prepared by disruption of cells with RIPA buffer (0.15 M NaCl, 0.5 tris-HCl, pH 7.2, 1% sodium deoxycholate, 0.1% SDS). The lysate is then centrifuged for 1 h. at 100,000 g. The lysate are reacted with 10 μl of the following test sera: lane 1--monoclonal anti-p24 (HTLV-III); lanes 2 and 3--human reference HTLV-III, positive serum; lane 4--human reference HTLV-III, negative serum; lanes 5 and 6--macaque reference STLV-III positive serum; lane 7--macaque reference STLV-III negative serum.

Figure 2:
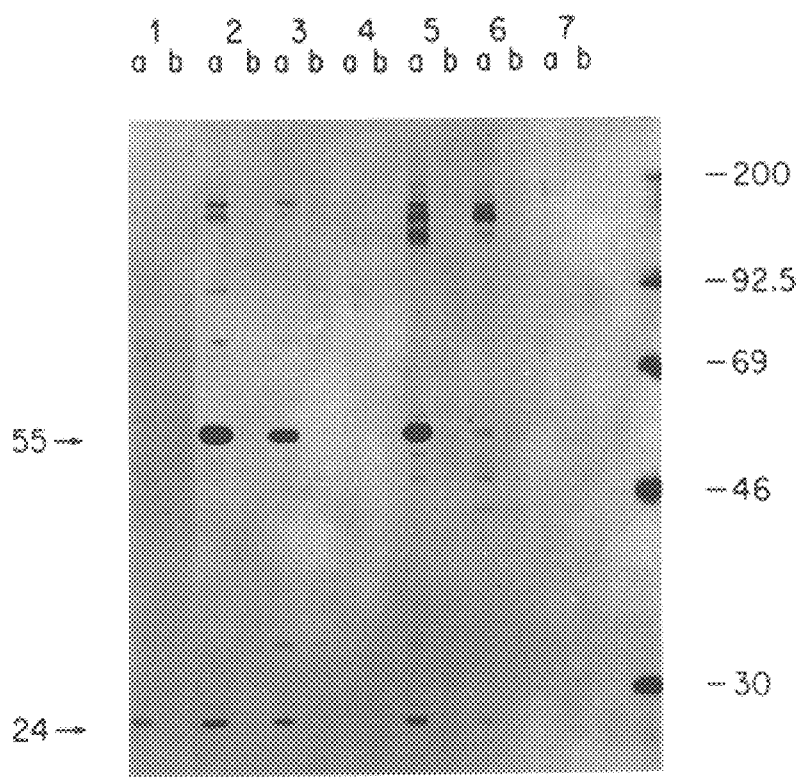

In both FIGS. 1 and 2, the STLV-III-infected macaque serum recognizes the gp120/gp160 protein of STLV-III$_{MAC}$-infected cells.

Example 3: Macaca STLV-III as determined by HTLV-III infected cells

Figure 3:
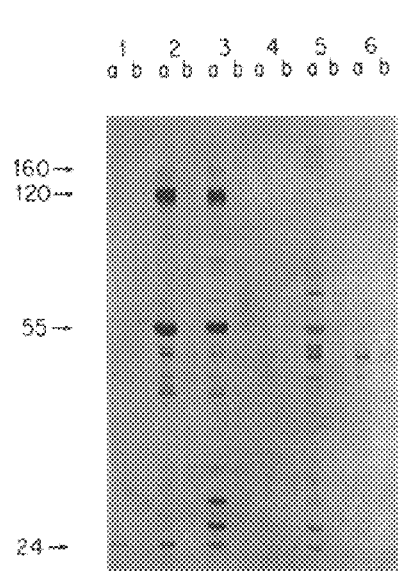

As shown in FIG. 3, the procedures described in example 2 were performed with HTLV-III-infected H9 cells using at lanes 1–5 the sera described for FIG. 2 at lanes 1–5 and using a representative macaque serum negative for STLV-III at lane 6.

Examples 4–6: STLV-III detected in Simians by STLV-III cell proteins

Figure 4:
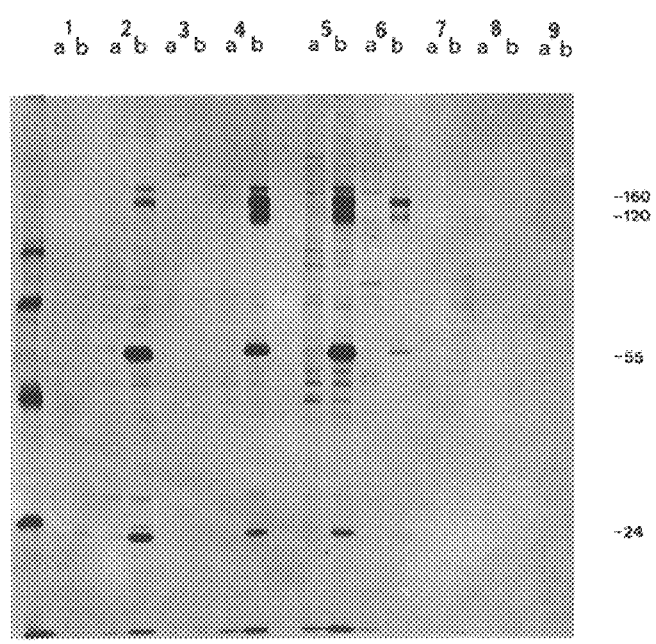

In FIG. 4, the above-described procedures were performed using HUT 78/STLV-III(a) and HUT 78(b) on the following serum samples: lane 1) monoclonal anti-p24 (HTLV-III); lane 2) human reference serum positive to HTLV-III; lane 3) human reference serum negative to HTLV-III; lane 4) macaque serum positive for STLV-III; lanes 5) and 6) AGM sera, positive for STLV-III; lane 7) AGM negative for STLV-III; lane 8) baboon serum negative for STLV-III; lane 9) chimpanzee serum negative for STLV-III. The 160, 120, 55, and 24 kd viral antigens of STLV-III are immunoprecipitated by positive macaque sera and by HTLV-III positive sera.

Figure 5:
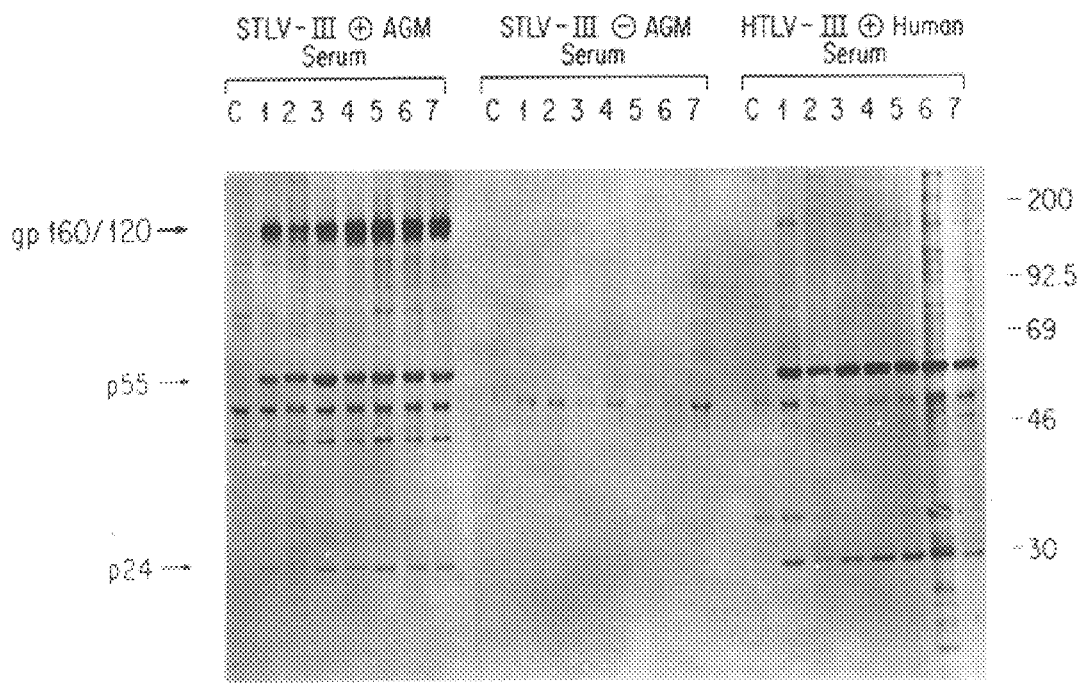

FIG. 5 demonstrates protein expression in seven different African green monkeys that are infected with STLV-III. Cell cultures from those monkeys were derived by cocultivation with HUT 78 cells. The cell cultures were metabolically labeled with $^{35}$S cysteine and RIP-SDS/PAGE of whole cell lysates was performed with: a) an STLV-III antibody positive AGM serum sample; b) an STLV-III antibody negative AGM serum sample; and c) and HTLV-III antibody positive reference serum sample from a human with AIDS-related complex. Lanes designated C represent HUT 78 uninfected cells that were similarly labeled.

Specifically, cells from the above-described cultures were exposed to [$^{35}$S] cysteine [–150 Ci/ml; specific activity 1000–1050 Ci/mmole; New England Nuclear (NEN)] for four to six hours. A soluble cell lysate was prepared by disrupting cells with RIPA buffer (0.15 M NaCl, 0.05 M Tris-HCl, pH7.2, 1% sodium deoxycholate, and 0.1% SDS), and clearing by centrifugation for one hour at 100,000 g. Each group of cell lysates were reacted with 10 µl of the test sera bound to Protein A-sepharose CL-4B (Proteins A-beads, Sigma). The immunoprecipitates were eluted in a sample buffer containing 0.1 M Cleland's reagent, 2% SDS, 0.08 M Tris-HCl, pH 6.8, 10% glycerol, and 0.2% bromophenol blue by boiling at 100° C. for two minutes. Samples were analyzed in a 10.0% acrylamide resolving gel with 3.5% stacking gel according to the discontinuous buffer system of Laemmli (1970) Nature 227:680

As shown in FIG. 5, lysates from all seven cultures (lanes 1–7) showed bands of about 160 kd, 120 kd, 55 kd, and 24 kd, when reacted with serum from a reference antibody positive African green monkey. The same bands were not seen with lysate from uninfected HUT 78 cells (lane C). The proteins were also not detected when lysates from the seven infected cell cultures were reacted with a representative serum from an African green monkey that lacked antibodies to STLV-III. Serum from a human ARC patient recognized the 55 kd and 24 kd proteins and had faint reactivity to proteins of about 120 kd and 160 kd in lysates prepared from isolates 1–7 but the same bands were lacking uninfected HUT 78 cells.

Figure 6:
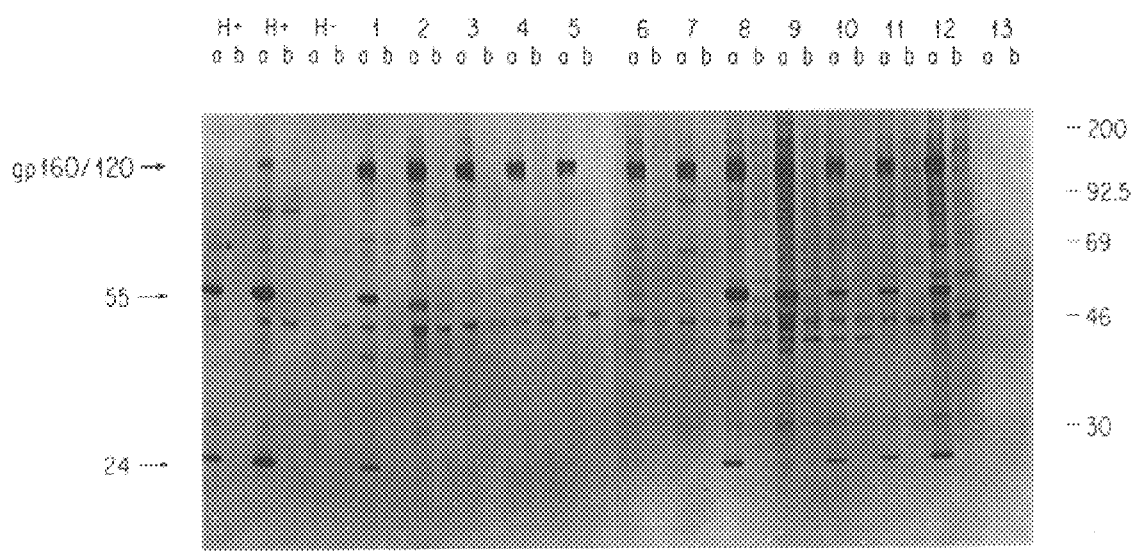

FIG. 6 shows immunoprecipitation by serum samples from the same seven different African green monkeys from which virus was successfully isolated were reacted with cell lysates prepared from an STLV-III$_{AGM}$ cell line (isolate 1) and uninfected HUT 78 cells (lanes 1–7). STLV-III$_{AGM}$ (isolate 1) infected (lanes a) and HUT 78 uninfected (lanes b) cell lysates were prepared as described above. Lanes H$^+$ contain serum samples from HTLV-III antibody positive human AIDS or ARC patients; lane H$^-$ contains a health control antibody negative human serum; lanes 1–7 are serum samples from African green monkeys from which virus isolates 1–7 were obtained; lanes 8–12 are serum samples from representative African green monkeys that were positive for antibodies to STLV-III$_{MAC}$, and lane 13 is a representative African green monkey serum that was negative for antibodies to STLV-III$_{MAC}$.

As shown in FIG. 6, sera from virus positive monkeys specifically precipitated the gp160/120, whereas only three of these serum samples additionally showed reactivity to the p55 and p24. Analysis of other African green monkeys sera has demonstrated a similar phenomenon where 11 of 42 (26%) STLV-III$_{AGM}$ positive serum samples showed reactivity to the p55 and p24 in addition to reactivity to the gp160/120. Thus, the high molecular weight glycoproteins of this virus apparently are the most immunogenic species in infected monkeys. STLV-III$_{AGM}$ positive sera from African green monkeys were also analyzed for antibodies to HTLV/III/LAV proteins by RIP/SDS-PAGE where approximately 50% of these sera also showed reactivity to HTLV-III proteins. Other diagnostic assays to detect this cross-reactivity reaction, in which the same serum samples were analyzed by ELISA to HTLV-III (Electronucleonics). STLV-III$_{AGM}$ virus and antibody positive monkeys demonstrated antibodies to HTLV-III proteins by RIP SDS/PADE in 5 of 8 serum samples whereas ELISA detected 2 of these 8 samples as HTLV-III positive. Thus, it appears that the presence of antibodies to STLV-III specific proteins was the most closely associated with virus isolation. RIP and SDS/PAGE analysis appear to be more sensitive for the detection of the cross-reacting antibodies to the related virus in infected monkeys when compared to the HTLV-III kit ELISA.

Example 7: Reactivity of HTLV-IV with HTLV-III and STLV-III

Serum samples from healthy individuals (prostitutes or surgery patients) were obtained in Dakar, Senegal, and screened by a commerically available HTLV-III/LAV ELISA kit assay. ELISA-positive samples were then analyzed by RIP/SDS/PAGE as generally described above, to eliminate false positives.

All positive samples demonstrated strong reactivity to all of the STLV-III viral antigens, including p24, p55, and gp120/gp160. Only 27% of the samples demonstrated reactivity to all HTLV-III/LAV antigens; some of the samples failed to demonstrate any detectable antibodies to any major HTLV-III/LAV antigens, while others possessed antibodies only to p24 and p55 gag-related antigens. In all cases the reactivity to HTLV-III gp120 and gp160 was weak or non-existent compared to reactivity to STLV-III gp120/160. And there was a lack of detectable antibodies to gp41 when analyzed by Western blot analysis by the general technique of Barin et al. Lancet, ii, pp. 1387 et seq. (1985).

Figure 7:
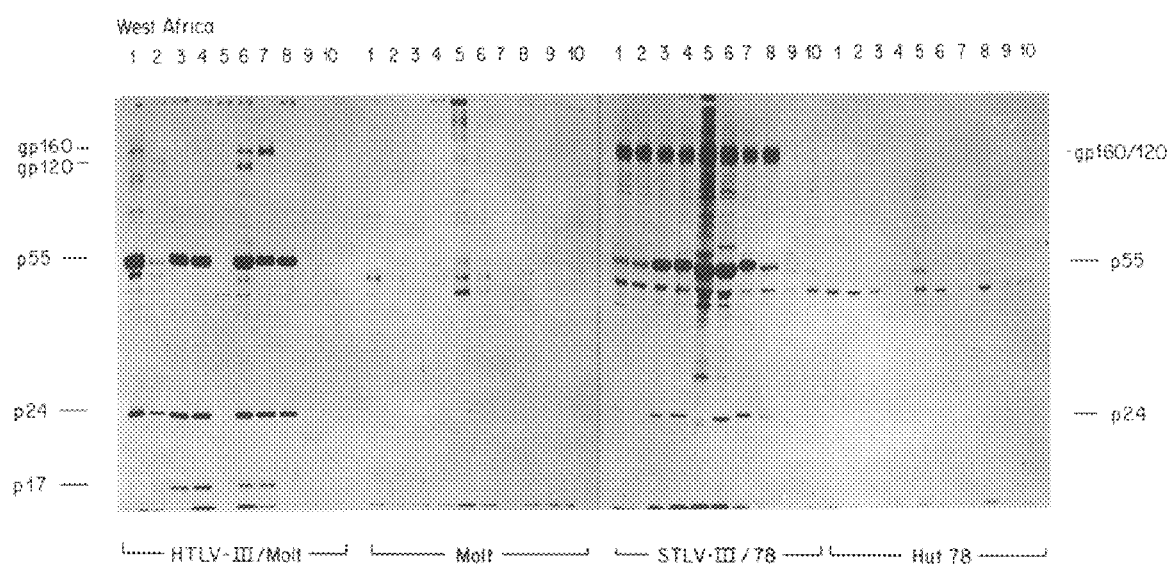

Representative serum samples from these West African individuals are shown in FIG. 7, with control serum samples from STLV-III antibody-positive African green monkeys.

Specifically, serum samples from people residing in West Africa were analyzed by RIP-SDS/PAGE using the whole cell lysates as follows. Cells from HTLV-III (BH10 virus) infected Molt-3 cells, uninfected Molt-3 cells, Hut-78 infected STLV-III$_{AGM}$, and uninfected Hut-78 cells were harvested at their peak of log phase of growth and were exposed to ($^{35}$S) cysteine (~150Ci/ml; specific activity 1000–1050 Ci/mmol; New England Nuclear (NEW) for 4–6 hours. A soluble cell lysate was prepared by disrupting cells with RIPA buffer (0.15 M NaCl, 0.05 M Tris-HCl, pH 7.2, 1% sodium deoxycholate, and 0.1% SDS), and clearing by centrifugation for 1 hour at 100,000 g. Each group of cell lysates were reacted with 10 μl of the following test sera bound to Protein A-Sepharose Cl-4B (Protein A-beads, Sigma); (Lanes 1–2) STLV-III$_{AGM}$ antibody positive African green monkeys; (lane 3) healthy West African control with antibodies to STLV-III$_{AGM}$; (lanes 4–8) sera from West African prostitutes with reactivity to STLV-III$_{AGM}$; (lane 9) STLV-III$_{AGM}$ and HTLV-III seronegative prostitute from West Africa; and (lane 10) healthy West African control seronegative for STLV-III$_{AGM}$ and HTLV-III.

Immunoprecipitates were eluted in a sample buffer containing 0.1 M Cleland's reagent, 2% SDS, 0.08 M Tris-HCl, pH 6.8, 10% glycerol, and 0.2% bromophenol blue by boiling at 100' for 2 mintues. Samples were analyzed in a 10.0% acrylamide resolving gel with 3.5% stacking gel according to the discontinuous buffer system of Laemmli referenced above.

Example 8: Isolation of HTLV-IV

To isolate HTLV-IV, peripheral blood lymphocytes were obtained from eight STLV-III$_{AGM}$ antibody positive people and were cocultivated with Hut-78 cells. The procedures for virus isolation was generally the same as that described above for STLV-III$_{AGM}$ or in Kanki et al. (1985) Science 230:951. Remarkably, the in vitro cytolysis of target cells was not observed. Therefore, Hut-78 cells were only added once to each culture at day 5. At 21 to 28 days in culture, cellular atypia and multinucleated giant cells were evident. Begining at 14 days after initiation, all cell cultures were monitored for viral protein expression by membrane immunofluoroescence (MIF) and RIP-SDS/PAGE as previously described, using a battery of reference sera with known antibody reactivity to STLV-III$_{AGM}$, HTLV-III/LAV, and HTLV-I viral proteins. After 28–35 days in culture, viral proteins related to STLV-III were detected in 3 cultures by both MIF and RIP-SDS/PAGE.

Cell-free supernatants from the 3 cultures were monitored for Mg+ dependent reverse transcriptase as previously described by Popovic et al. (1984) Science 224:497 and Salahudin et al. (1984) Science 224:500. 3,500–93,000 counts per minute (cpm) over background (76–860 cpm) was observed in the 3 cell cultures expressing STLV-III viral proteins and not in cultures that were negative for viral proteins.

Cell cultures expressing antigens cross reactive with STLV-III were examined by electron microscopy. Particles characteristic of a retrovirus were observed budding from infected cell membranes. Extracellular virions demonstrated an electron-dense cylindrical core, similar to that described for both simian and human T-lymphotrophic viruses. The ultrastructural morphology of retroviral particles seen in all three cultures derived from STLV-III antibody positive people of West Africa were similar to the retroviral particles of a reference STLV-III$_{AGM}$ cell line derived from an African green monkey. It is notable that the spike proteins of STLV-III type virions from both monkey and human origin were more prominent than those usually obserbed with HTLV-III/LAV virions. The level of virus production from the West African STLV-III related virus culture was similar to that observed with HTLV-III/LAV infected H9 cells, based on both visual examination and reverse transcriptase activity.

Example 9: Identification of Antigens of HTLV-IV

Figure 8:
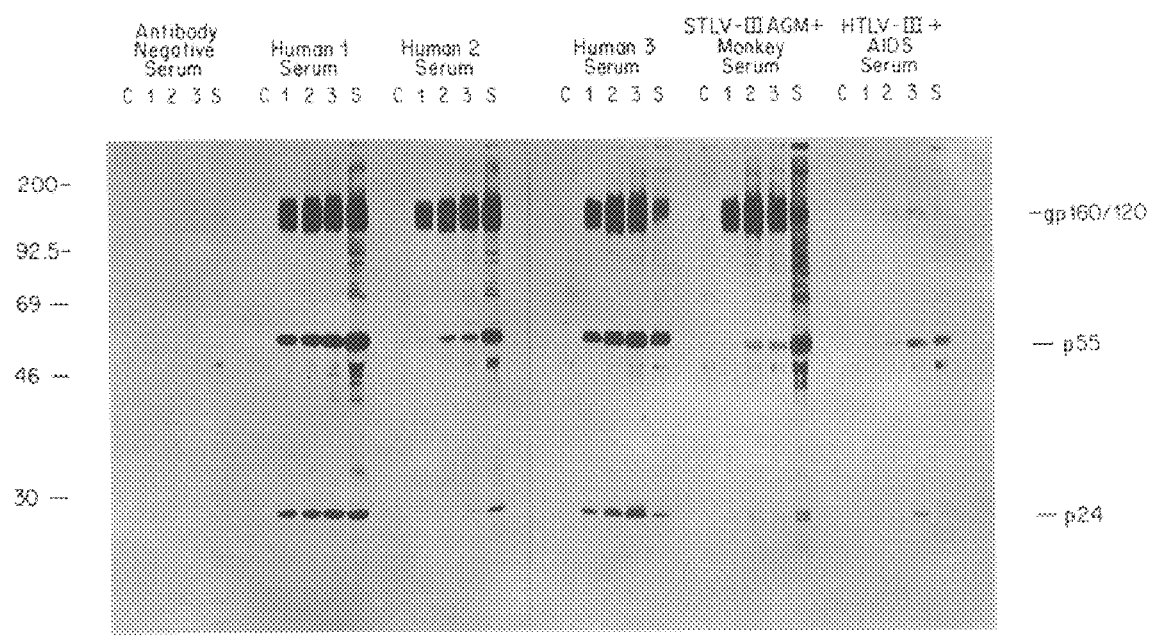

As shown in FIG. 8, whole cell lysates from three HTLV-IV cell cultures (lanes 1–3), STLV-III$_{AGM}$ reference infected Hut-78 (S) and uninfected Hut-78 cells (C) were prepared as described above and analyzed by RIP-SDS/PAGE as follows. Each group of cell lysates were reacted with the following test sera: Negative serum sample from West Africa, virus and antibody negative for STLV-III and HTLV-III, STLV-III antibody positive serum from individual 1, HTLV-III antibody positive serum from individual 2, STLV-III antibody positive serum from individual 3, reference STLV-III antibody positive serum from an African green monkey, and reference HTLV-III antibody positive serum from an AIDS patient.

Serum from a negative control individual that lacked antibodies to both STLV-III and HTLV-III/LAV failed to recognize any specific proteins in any of the five lysates. Conversely, lysates from STLV-III-positive cultures 1, 2, and 3 demonstrated bands of about 160, 129, 55 and 24 kd when reacted with their own sera or serum from a reference STLV-III antibody positive African green monkey (lanes 1, 2, and 3). These bands were indistinguishable from proteins with similar electrophoretic mobility precipitated from reference STLV-III$_{AGM}$ whole cel lysate (lanes S). These bands were not detectable when the same sera reacted with uninfected Hut-78 cell lysates (lane C) or similarly prepared whole cell lysates from cultures derived from antibody negative people from West Africa. Serum from a reference U.S. AIDS patient recognized the 55 and 24 kd proteins of STLV-III$_{AGM}$ and reacted similarly with the same proteins in cultures 1–3; only faint reactivity to the high molecular weight proteins, gp120/160, was observed.

Figure 9:
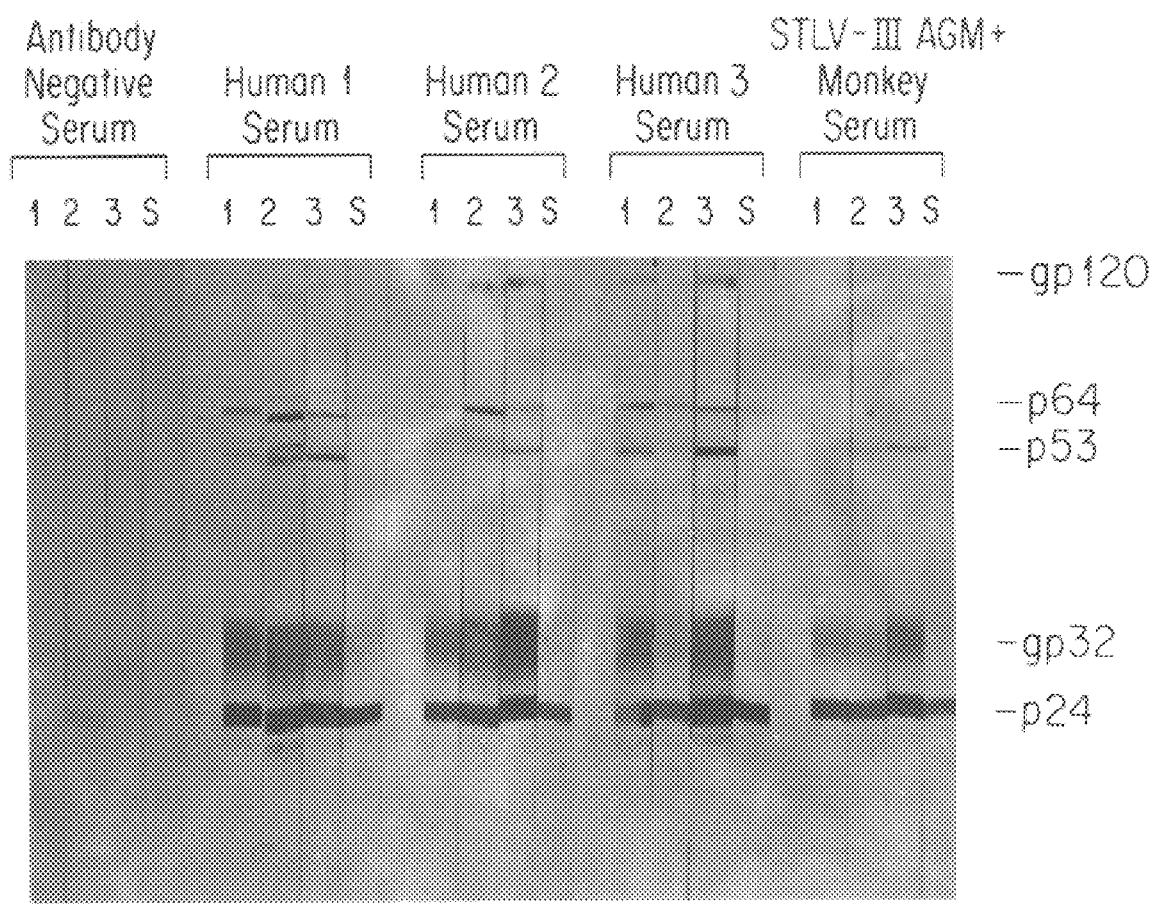

As shown in FIG. 9, the viral antigens of STLV-III$_{AGM}$ recognized by the Western blot procedure include the p24, p15, p53, p64, gp120 and gp32. p24 and p15 are gag-related and analogous to similar viral proteins of HTLV-III/LAV. A 120 kd protein has been demonstrated with some STLV-III and HTLV-IV antibody positive serum samples; this protein is though to be analogous to the HTLV-III/LAV gp120 which is less frequently detected by Western blot procedures but readily detected by HTLV-III/LAV antibody positive samples by RIP-SDS/PAGE. The smearing band at 32 kd using the Western blot technique of Barin et al. Lancet ii, p. 1387 (1987) correlates with a similar appearing 32 kd glycoprotein observed with lentil-lectin preparations and RIP-SDS/PAGE. The p32 protein may represent the transmembrane glycoprotein of STLV-III$_{AGM}$ and HTLV-IV, by analogy with the gp41 of HTLV-III/LAV. The p64 and p53 of STLV-III$_{AGM}$ and HTLV-IV are analogous to two pol gene products of HTLV-III/LAV, p53 and p64.

Western blots can be performed as demonstrated by the following example. Cell-free virus from culture 1–3 as well as STLV-III$_{AGM}$ virus from a reference cell line was collected from supernatant fluid and subjected to Western blotting by the general technique of Barin et al. Strips were incubated with the same serum samples described in connection with FIG. 8. STLV-III$_{AGM}$ antibody positive reference serum from an African green monkey showed reactivity with gp32, p24, p53, and p64 of STLV-III$_{AGM}$ as well as similar bands in the three virus preparation from prostitutes from West Africa (FIG. 9). Similar proteins were recognized using serum samples from individuals that had yielded STLV-III related viruses (HTLV-IV) with some variability in recognition to the gp120. Control antibody negative serum failed to detect these bands in any of the four virus preparations.

As shown in FIG. 9, Western blot analysis was performed on virus preparations of the 3 HTLV-IV cell cultures (lanes 1–3), and an STLV-III$_{AGM}$ reference infected cell line (S). Each group of strips were reacted with: Negative serum sample from West Africa, virus and antibody negative for STLV-III and HTLV-III, STLV-III antibody positive serum from individual 1, STLV-III antibody positive serum from individual 2, STLV-III antibody positive serum from individual 3, and reference STLV-III antibody positive serum from an African green monkey.

IV. Vaccine

Since STLV-III$_{AGM}$ and HTLV-IV are immunologically cross-reactive with HTLV-III, and yet present data indicates reduced (or no) pathenogenicity in their respective hosts. STLV-III$_{AGM}$, HTLV-IV or a portion or derivative thereof could be used as a vaccine to protect against HTLV-III.

Specifically, using tryptic peptide analysis of the STLV-III$_{AGM}$ or HTLV-IV peptide antigens, it is possible to determine the antigenic determinants which cross react with HTLV-III. Polypeptides that include these determinants can be synthesized, using organisms or cells engineered by recombinant DNA techniques. The resulting polypeptides can be recovered and included in a pharmaceutically acceptable carrier to innoculate individuals to raise protection against HTLV-III infection. Specifically, the conserved epitopes of the env proteins of STLV-III and HTLV-IV are candidate immunogens for HTLV-III/LAV vaccine development. U.S. Ser. No. 06/790,830, filed Oct. 23 or 24, 1985 by Kennedy, Dreesman and Essex, entitled Synthetic Peptides and Use for Diagnosis and Vaccination for AIDS and ARC, is hereby incorporated by reference in its entirety and discloses one method that could be used to derive a vaccine based on polypeptide antigens of STLV-III or HTLV-IV.

What is claimed is:

1. An isolated polypeptide selected from the group consisting of:
    (a) a cell-surface glycoprotein of m.w. of about 160,000;
    (b) a cell-surface glycoprotein of m.w. of about 120,000;
    (c) a gag protein of m.w. of about 55,000;
    (d) a gag protein of m.w. of about 24,000; and
    (e) a glycoprotein of m.w. of about 32,000;
    wherein the polypeptide has said molecular weight when produced by a cell infected with a strain of an HIV-2 virus, wherein the cell infected with a strain of the HIV-2 virus is a cell deposited as ATCC VR2129, and wherein the polypeptide is not an HIV-1 polypeptide having the same molecular weight as the isolated polypeptide.

2. The polypeptide of claim 1, wherein said infected cell is a progeny of one of the cell lines deposited as ATCC VR2129.

3. A cell lysate comprising a cell-surface glycoprotein of m.w. of about 160,000 that has an antigenic determinant which, in common with an antigenic determinant of a protein produced by a cell infected with a strain of an HIV-2 virus, will react with a same given antibody, wherein the cell infected with a strain of an HIV-2 virus is a cell deposited as ATCC VR2129, and wherein the glycoprotein is not an HIV-I polypeptide having a m.w. of about 160,000.

4. The cell lysate of claim 3, comprising a cell-surface glycoprotein of m.w. of about 120,000 that has an antigenic determinant which, in common with an antigenic determinant of a protein produced by a cell infected with a strain of an HIV-2 virus, will react with a same given antibody, wherein the cell infected with a strain of an HIV-2 virus is a cell deposited as ATCC VR2129, and wherein the glycoprotein of m.w. of 120,000 is not an HIV-I polypeptide having a m.w. of about 120,000.

5. The cell lysate of claim 4, comprising a gag protein of m.w. of about 55,000 that has an antigenic determinant which, in common with an antigenic determinant of a protein produced by a cell infected with a strain of a HIV-2 virus, will react with a same given antibody, wherein the cell infected with a strain of an HIV-2 virus is a cell deposited as ATCC VR2129, and wherein the gag protein of m.w. of about 55,000 is not an HIV-I polypeptide having a m.w. of about 55,000.

6. The cell lysate of claim 5, comprising a gag protein of m.w. of about 24,000 that has an antigenic determinant which, in common with an antigenic determinant of a protein produced by a cell infected with a strain of an HIV-2 virus, will react with a same given antibody, wherein the cell infected with a strain of an HIV-2 virus is a cell deposited as ATCC VR2129, and wherein the glycoprotein of m.w. of about 24,000 is not an HIV-I polypeptide having a m.w. of about 24,000.

7. The cell lysate of claim 6, comprising a glycoprotein of m.w. of about 32,000 that has an antigenic determinant which, in common with an antigenic determinant of a protein produced by a cell infected with a strain of an HIV-2 virus, will react with a same given antibody, wherein the cell infected with a strain of an HIV-2 virus is a cell deposited as ATCC VR2129, and wherein the glycoprotein of m.w. of about 32,000 is not an HIV-I polypeptide having a m.w. of about 32,000.

8. An isolated cell-surfce glycoprotein of m.w. of about 160 kD that has an antigenic determinant which, in common with an antigenic determinant of a protein also having a m.w. of about 160 kD produced by a cell infected with a strain of an HIV-2 virus, will react with a same given antibody, wherein the cell infected with a strain of an HIV-2 virus is a cell deposited as ATCC VR2129, and wherein the glycoprotein is not a 160 kD protein of HIV-I.

9. An isolated cell-surface glycoprotein of m.w. of about 120 kD that has an antigenic determinant which, in common with an antigenic determinant of a protein also having a m.w. of about 120 kD produced by a cell infected with a strain of an HIV-2 virus, will react with a same given antibody, wherein the cell infected with a strain of an HIV-2 virus is a cell deposited as ATCC VR2129, and wherein the glycoprotein is not a 120 kD protein of HIV-I.

10. An isolated gag protein of m.w. of about 55 kD that has an antigenic determinant which, in common with an antigenic determinant of a protein also havig a m.w. of about 55 kD produced by a cell infected with a strain of an HIV-2 virus, will react with the same given antibody, wherein the cell infected with a strain of an HIV-2 virus is a cell deposited as ATCC VR2129, and wherein the gag protein is not a 55 kD protein of HIV-I.

11. An isolated gag protein of m.w. of about 24 kD that has an antigenic determinant which, in common with an antigenic determinant of a protein also havig a m.w. of about 24 kD produced by a cell infected with a strain of an HIV-2 virus, will react with the same given antibody, wherein the cell infected with a strain of an HIV-2 virus is a cell deposited as ATCC VR2129, and wherein the gag protein is not a 24 kD protein of HIV-I.

12. An isolated glycoprotein of m.w. of about 32 kD that has an antigenic determinant which, in common with an antigenic determinant of a protein also havig a m.w. of about 32 kD produced by a cell infected with a strain of an HIV-2 virus, will react with a same given antibody, wherein the cell infected with a strain of an HIV-2 virus is a cell deposited as ATCC VR2129, and wherein the glyco protein is not a 32 kD protein of HIV-I.

13. An isolated polypeptide of claim 1, wherein said polypeptide is selected from the group consisting of:

(a) a gag protein of m.w. of about 55,000; and (b) a gag protein of m.w. of about 24,000.

* * * * *